US012004926B2

(12) United States Patent
Long et al.

(10) Patent No.: US 12,004,926 B2
(45) Date of Patent: Jun. 11, 2024

(54) WOUND DRESSINGS AND SYSTEMS WITH REMOTE OXYGEN GENERATION FOR TOPICAL WOUND THERAPY AND RELATED METHODS

(71) Applicants: KCI LICENSING, INC., San Antonio, TX (US); KCI USA, INC., San Antonio, TX (US)

(72) Inventors: Justin Alexander Long, San Antonio, TX (US); Christopher Brian Locke, Bournemouth (GB); Alexander Waite, Keighley (GB)

(73) Assignees: KCI Licensing, Inc., San Antonio, TX (US); KCI USA, Inc., San Antonio, TX (US)

( * ) Notice: Subject to any disclaimer, the term of this patent is extended or adjusted under 35 U.S.C. 154(b) by 561 days.

(21) Appl. No.: 16/648,308

(22) PCT Filed: Sep. 18, 2018

(86) PCT No.: PCT/US2018/051408
§ 371 (c)(1),
(2) Date: Mar. 18, 2020

(87) PCT Pub. No.: WO2019/055954
PCT Pub. Date: Mar. 21, 2019

(65) Prior Publication Data

US 2020/0282114 A1 Sep. 10, 2020

Related U.S. Application Data

(60) Provisional application No. 62/559,789, filed on Sep. 18, 2017.

(51) Int. Cl.
*A61F 13/05* (2024.01)
*A61M 1/00* (2006.01)

(52) U.S. Cl.
CPC ............... *A61F 13/05* (2024.01); *A61M 1/85* (2021.05); *A61M 1/915* (2021.05); *A61M 1/94* (2021.05);
(Continued)

(58) Field of Classification Search
CPC ................................................. A61F 13/00068
See application file for complete search history.

(56) References Cited

U.S. PATENT DOCUMENTS

| | | | | |
|---|---|---|---|---|
| 2003/0050674 A1 | 3/2003 | Joshi | | |
| 2004/0030304 A1* | 2/2004 | Hunt | A61F 13/00068 604/317 | |

(Continued)

FOREIGN PATENT DOCUMENTS

| | | |
|---|---|---|
| CN | 205924317 | 2/2017 |
| EP | 2956101 | 12/2015 |

(Continued)

OTHER PUBLICATIONS

International Search Report and Written Opinion issued in Corresponding PCT Application No. PCT/US2018/051408, dated Jan. 23, 2019.

(Continued)

*Primary Examiner* — Benjamin J Klein
*Assistant Examiner* — Meagan Ngo

(57) ABSTRACT

This disclosure includes wound dressings and systems with remote oxygen generation for topical wound therapy and related methods. Some systems include a dressing for facilitating delivery of oxygen to the target tissue, the dressing having: a first manifold that defines a plurality of gas passageways and is configured to allow communication of oxygen to the target tissue; a gas-occlusive layer configured to be disposed over the first manifold and coupled to tissue surrounding the target tissue such that: an interior volume is
(Continued)

defined between the gas-occlusive layer and the target tissue; and the gas-occlusive layer limits escape of oxygen from the interior volume between the gas-occlusive layer and the tissue surrounding the target tissue; a container outside the interior volume, the container having a sidewall that defines a chamber configured to be in fluid communication with the interior volume; and an oxygen-generating material disposed within the chamber of container and configured to release oxygen when exposed to water.

5 Claims, 6 Drawing Sheets

(52) U.S. Cl.
CPC ..... *A61M 1/964* (2021.05); *A61M 2202/0208* (2013.01); *A61M 2205/7536* (2013.01)

(56) References Cited

U.S. PATENT DOCUMENTS

| | | | | |
|---|---|---|---|---|
| 2004/0260253 | A1 | 12/2004 | Rosati | |
| 2006/0200100 | A1 | 9/2006 | Rosati | |
| 2009/0227969 | A1 | 9/2009 | Jaeb et al. | |
| 2009/0259171 | A1 | 10/2009 | Joshi et al. | |
| 2010/0069858 | A1 | 3/2010 | Olson | |
| 2010/0159192 | A1* | 6/2010 | Cotton | A61L 15/58 428/137 |
| 2010/0305490 | A1 | 12/2010 | Coulthard et al. | |
| 2012/0059301 | A1 | 3/2012 | Franklin | |
| 2012/0143113 | A1* | 6/2012 | Robinson | A61M 1/964 604/319 |
| 2012/0209226 | A1 | 8/2012 | Simmons et al. | |
| 2016/0030722 | A1* | 2/2016 | Anderson | A61M 1/73 604/20 |
| 2016/0166781 | A1 | 6/2016 | Sarangapani et al. | |
| 2016/0175500 | A1 | 6/2016 | Cali et al. | |
| 2017/0319394 | A1 | 11/2017 | Chen et al. | |
| 2019/0030224 | A1* | 1/2019 | Lin | A61L 15/26 |
| 2019/0030226 | A1* | 1/2019 | Lin | A61L 15/44 |

FOREIGN PATENT DOCUMENTS

| | | |
|---|---|---|
| TW | 200942281 | 10/2009 |
| TW | M525742 | 7/2016 |
| WO | WO 1996/032082 | 10/1996 |
| WO | WO 2009/066106 | 5/2009 |
| WO | WO 2009/097534 | 8/2009 |
| WO | WO 2009/146441 | 12/2009 |
| WO | WO 2009/158500 | 12/2009 |
| WO | WO 2011/008497 | 1/2011 |
| WO | WO 2011/008711 | 1/2011 |
| WO | WO 2013/066694 | 5/2013 |
| WO | WO 2014/144762 | 9/2014 |
| WO | WO 2015/123353 | 8/2015 |

OTHER PUBLICATIONS

International Search Report and Written Opinion issued in Corresponding PCT Application No. PCT/US2018/052137, dated Dec. 19, 2018.

International Search Report and Written Opinion issued in Corresponding PCT Application No. PCT/US2019/012250, dated May 7, 2019.

International Search Report and Written Opinion issued in Corresponding PCT Application No. PCT/US2019/012273, dated May 16, 2019.

International Search Report and Written Opinion Issued in Corresponding PCT Patent Application No. PCT/US2018/057214, dated Jan. 31, 2019.

* cited by examiner

WOUND DRESSINGS AND SYSTEMS WITH REMOTE OXYGEN GENERATION FOR TOPICAL WOUND THERAPY AND RELATED METHODS

CROSS-REFERENCE TO RELATED APPLICATIONS

This application is a national phase application under 35 U.S.C. § 371 of International Application No. PCT/US2018/051408, filed Sep. 18, 2018, which claims the benefit of U.S. Provisional Application No. 62/559,789, filed Sep. 18, 2017, the contents of which applications are incorporated herein in their entirety.

BACKGROUND

1. Field of Invention

The present invention relates generally to wound dressings, and more specifically, but not by way of limitation, to wound dressings and systems with remote oxygen generation for topical wound therapy and related methods.

2. Description of Related Art

Clinical studies and practice have shown that topical applications of therapeutic oxygen can improve wound healing, especially in chronic wounds. Topical applications of therapeutic oxygen can reduce tissue inflammation and/or improve tissue proliferation (e.g., improve collagen synthesis, growth factor production, angiogenesis, and/or the like).

Traditional oxygen-based therapies deliver oxygen with the use of hyperbaric oxygen chambers, oxygen concentrating devices, continuously-diffusing oxygen generating devices, and animal-derived hemoglobin. These traditional oxygen-based therapies offer relatively short treatment periods, reduce patient mobility, and/or require investment in expensive equipment and/or proprietary wound dressings.

While the clinical benefits of topical applications of therapeutic oxygen are known, reductions in the expense and/or improvements to the efficacy, simplicity, and/or mobility of therapy systems, components, and related methods may benefit healthcare providers and patients.

SUMMARY

One or more embodiments of the present dressings, systems, and/or methods can provide greater efficacy and/or accuracy in the delivery and/or monitoring of the topical application of therapeutic oxygen to target tissue.

Some embodiments of the present dressings for facilitating delivery of oxygen to target tissue comprise a manifold that defines a plurality of gas passageways and is configured to allow communication of oxygen to the target tissue; a gas-occlusive layer configured to be disposed over the manifold and coupled to tissue surrounding the target tissue such that: an interior volume is defined between the gas-occlusive layer and the target tissue; and the gas-occlusive layer limits escape of oxygen from the interior volume between the gas-occlusive layer and the tissue surrounding the target tissue; and a port coupled to the gas-occlusive layer, wherein the port is configured to be releasably coupled to an oxygen-generating device and to allow fluid communication of oxygen between the oxygen-generating device and the interior volume.

In some embodiments of the present dressings, the oxygen-generating device comprises a container outside the interior volume, the container having a sidewall that defines a chamber configured to be in fluid communication with the interior volume.

In some embodiments of the present dressings, an oxygen-generating material is disposed within the chamber of the container and configured to release oxygen when exposed to water.

In some embodiments of the present dressings, the port is configured to be releasably coupled to the oxygen-generating device such that the oxygen-generating device can be decoupled from the port without removing the dressing from the tissue surrounding the target tissue. In some embodiments of the present dressings, the port is configured to allow communication of oxygen into the interior volume through the port and allow communication of exudate out of the interior volume through the port.

Some embodiments of the present dressings comprise a filter configured to filter fluid that flows through the port. In some embodiments of the present dressings, the filter comprises a layer of material that is bonded to an upper surface or a lower surface of the gas-occlusive layer. In some embodiments of the present dressings, the filter is configured to allow communication of oxygen into the interior volume through the port and restrict communication of exudate out of the interior volume through the port. In some embodiments of the present dressings, the filter is configured to provide a viral and/or bacterial barrier.

Some embodiments of the present dressings comprise a liquid control layer having a plurality of perforations, the liquid control layer configured to be disposed between the manifold and the target tissue to restrict communication of exudate toward the target tissue. In some embodiments of the present dressings, the liquid control layer comprises a foam or a non-woven textile. In some embodiments of the present dressings, the liquid control layer comprises a hydrophilic material, optionally, a superabsorbent polymer. In some embodiments of the present dressings, the liquid control layer comprises a film. In some embodiments of the present dressings, the liquid control layer includes an opening and at least a portion of the port overlies at least a portion of the opening of the liquid control layer.

In some embodiments of the present dressings, the manifold includes an opening and at least a portion of the port overlies at least a portion of the opening of the manifold.

In some embodiments of the present dressings, the port extends through the opening of the manifold to guide the communication of oxygen into the interior volume. In some embodiments of the present dressings, the port extends through the opening of the liquid control layer to guide the communication of oxygen into the interior volume.

Some embodiments of the present dressings comprise a patient-interface layer configured to be disposed below the liquid control layer and in contact with the tissue surrounding the target tissue, the patient-interface layer defining a plurality of openings configured to allow communication of oxygen and exudate through the patient-interface layer. In some embodiments of the present dressings, the patient-interface layer comprises a polymer, optionally, silicone, polyethylene, ethylene vinyl acetate, a copolymer thereof, or a blend thereof. In some embodiments of the present dressings, the patient-interface layer includes an adhesive configured to couple the patient-interface layer to the tissue.

Some embodiments of the present dressings comprise a sorbent material configured to be disposed above or below the manifold and to capture exudate. Some embodiments of the present dressings comprise a sorbent layer that includes the sorbent material.

In some embodiments of the present dressings, the sorbent layer has a plurality of perforations; the sorbent layer has a plurality of openings; and/or the sorbent layer has a textured surface comprising a plurality of grooves.

In some embodiments of the present dressings, a planform area of the sorbent layer is at least 5 percent smaller than a planform area of the manifold.

In some embodiments of the present dressings, the sorbent layer comprises an absorbent material. In some embodiments of the present dressings, the absorbent material comprises a foam, a non-woven textile, or a superabsorbent polymer. In some embodiments of the present dressings, the sorbent layer comprises an adsorbent material. In some embodiments of the present dressings, the adsorbent material comprises a carbon filter.

In some embodiments of the present dressings, the manifold comprises a foam or a non-woven textile. In some embodiments of the present dressings, the manifold comprises polyethylene, a polyolefin, a polyether, polyurethane, a co-polyester, a copolymer thereof, or a blend thereof.

In some embodiments of the present dressings, the gas-occlusive layer comprises polyurethane, polyethylene, polyvinyl acetate, polyvinyl chloride, polyvinylidene chloride, isobutylene, a halogenated isomer, a copolymer thereof, or a blend thereof. In some embodiments of the present dressings, the gas-occlusive layer comprises an oxygen permeability coefficient ranging from 0.0003 to 0.001. In some embodiments of the present dressings, the gas-occlusive layer comprises a moisture vapor transmission rate (MVTR) of at least 250 grams per meters squared per day (g/m2/day). In some embodiments of the present dressings, the gas-occlusive layer comprises an adhesive configured to couple the gas-occlusive layer to tissue surrounding the target tissue. In some embodiments of the present dressings, the adhesive comprises an acrylic adhesive, polyurethane gel adhesive, silicone adhesive, or a combination thereof.

Some embodiments of the present systems for facilitating delivery of oxygen to the target tissue comprise a dressing having: a first manifold that defines a plurality of gas passageways and is configured to allow communication of oxygen to the target tissue; a gas-occlusive layer configured to be disposed over the first manifold and coupled to tissue surrounding the target tissue such that: an interior volume is defined between the gas-occlusive layer and the target tissue; and the gas-occlusive layer limits escape of oxygen from the interior volume between the gas-occlusive layer and the tissue surrounding the target tissue; a container outside the interior volume, the container having a sidewall that defines a chamber configured to be in fluid communication with the interior volume; and an oxygen-generating material disposed within the chamber of container and configured to release oxygen when exposed to water.

In some embodiments of the present systems, the oxygen-generating material comprises an adduct of hydrogen peroxide. In some embodiments of the present systems, the adduct comprises sodium percarbonate and/or hydrogen peroxide-urea.

Some embodiments of the present systems comprises a competitive agent disposed within the chamber of the container, the competitive agent configured to limit the communication of oxygen between the chamber of the container and the interior volume of the dressing. In some embodiments of the present systems, the competitive agent includes sodium carbonate. In some embodiments of the present systems, the competitive agent comprises a second sorbent material disposed within the chamber of the container, the second sorbent material configured to capture water within the chamber. In some embodiments of the present systems, the second sorbent material comprises an absorbent material. In some embodiments of the present systems, the absorbent material comprises a foam, a non-woven textile, or a superabsorbent polymer. In some embodiments of the present systems, the second sorbent material comprises an adsorbent material. In some embodiments of the present systems, the adsorbent material comprises a carbon filter.

In some embodiments of the present systems, the chamber of the container includes one or more capsules, each of which define a pocket that includes water. In some embodiments of the present systems, flexion of a portion of at least one of the one or more capsules causes the capsule to release water from within the pocket. In some embodiments of the present systems, at least one of the one or more capsules comprises polyethylene, polyether, polyurethane, a co-polyester, a co-polymer, a blend thereof, or a foil film or laminate.

Some embodiments of the present systems comprise a water reservoir outside the chamber of the container, the water reservoir configured to be in fluid communication with the chamber.

Some embodiments of the present systems comprise a second manifold disposed within the chamber, the oxygen-generating material disposed above and coupled to the second manifold.

In some embodiments of the present systems, the second manifold comprises a foam or a non-woven textile. In some embodiments of the present systems, the second manifold comprises polyethylene, a polyolefin, a polyether, polyurethane, a co-polyester, a copolymer thereof, or a blend thereof.

In some embodiments of the present systems, the oxygen generating material is coupled to the second manifold by an adhesive.

In some embodiments of the present systems, the competitive agent includes the adhesive.

In some embodiments of the present systems, the dressing comprises a liquid control layer having a plurality of perforations, the liquid control layer configured to be disposed between the first manifold and the target tissue to restrict communication of exudate toward the target tissue. In some embodiments of the present systems, the liquid control layer comprises a foam or a non-woven textile. In some embodiments of the present systems, the liquid control layer comprises a hydrophilic material, optionally, a superabsorbent polymer. In some embodiments of the present systems, the liquid control layer comprises a film.

In some embodiments of the present systems, the dressing comprises a port coupled to the gas-occlusive layer, the port configured to permit fluid communication between the chamber of the container and the interior volume of the dressing. In some embodiments of the present systems, the port is configured to allow communication of oxygen into the interior volume through the port and permit communication of exudate out of the interior volume through the port.

In some embodiments of the present systems, the dressing comprises a filter configured to filter fluid that flows through the port. In some embodiments of the present systems, the filter comprises a layer of material that is bonded to an upper surface or a lower surface of the gas-occlusive layer. In some embodiments of the present systems, the filter is configured to allow communication of oxygen into the interior volume through the port and restrict communication of exudate out of the interior volume through the port. In some embodiments of the present systems, the filter is configured to provide a viral and/or bacterial barrier.

In some embodiments of the present systems, the first manifold includes an opening and at least a portion of the port overlies at least a portion of the opening of the first manifold. In some embodiments of the present systems, the liquid control layer includes an opening and at least a portion of the port overlies at least a portion of the opening of the liquid control layer. In some embodiments of the present systems, the port extends through the opening of the first manifold to guide the communication of oxygen into the interior volume. In some embodiments of the present systems, the port extends through the opening of the liquid control layer to guide the communication of oxygen into the interior volume.

Some embodiments of the present systems comprise a conduit configured to be coupled between the container and the dressing to permit fluid communication between the chamber of the container and the interior volume of the dressing. In some embodiments of the present systems, the conduit is configured to be releasably coupled to the port and/or to the container such that the container can be decoupled from the dressing without removing the dressing from the tissue surrounding the target tissue. In some embodiments of the present systems, the conduit includes: an elongated core comprising a third manifold having a foam or a non-woven textile; and a sheath comprising a gas-occlusive film; wherein the sheath is disposed around and extends along at least a majority of a length of the core. In some embodiments of the present systems, the third manifold comprises a hydrophilic material, optionally, a superabsorbent polymer. In some embodiments of the present systems, the third manifold comprises polyethylene, a polyolefin, a polyether, polyurethane, a co-polyester, a copolymer thereof, or a blend thereof. In some embodiments of the present systems, the sheath comprises polyurethane, polyethylene, polyvinyl acetate, polyvinyl chloride, polyvinylidene chloride, isobutylene, a halogenated isomer, a copolymer thereof, or a blend thereof.

Some embodiments of the present systems comprise a negative pressure source configured to be in fluid communication with the chamber of the container such that the negative pressure source provides sub-atmospheric pressure within the chamber.

Some embodiments of the present systems comprise a valve coupled to the gas-occlusive layer of the dressing and configured to relieve pressure within the interior volume when pressure within the interior volume exceeds a threshold pressure. In some embodiments of the present systems, the valve comprises a one-way valve configured to: permit communication of gas out of the interior volume through the valve; and prevent communication of gas into the interior volume through the valve.

In some embodiments of the present systems, the sidewall of the container includes a resealable opening to allow access to the chamber.

Some embodiments of the present systems comprise a patient-interface layer configured to be disposed within the interior volume and to be in contact with the tissue surrounding the target tissue, the patient-interface layer defining a plurality of openings configured to allow communication of oxygen and exudate through the patient-interface layer.

Some embodiments of the present systems comprise a first sorbent material configured to be disposed within the interior volume of the dressing and above or below the first manifold and to capture exudate. Some embodiments of the present systems comprise a first sorbent layer that includes the first sorbent material.

In some embodiments of the present systems, the first sorbent layer has a plurality of perforations; the first sorbent layer has a plurality of openings; and/or the first sorbent layer has a textured surface comprising a plurality of grooves. In some embodiments of the present systems, a planform area of the first sorbent layer is at least 5 percent smaller than a planform area of the first manifold. In some embodiments of the present systems, the first sorbent layer comprises an absorbent material. In some embodiments of the present systems, the absorbent material comprises a foam, a non-woven textile, or a superabsorbent polymer. In some embodiments of the present systems, the sorbent layer comprises an adsorbent material. In some embodiments of the present systems, the adsorbent material comprises a carbon filter.

In some embodiments of the present systems, the patient-interface layer comprises a polymer, optionally, silicone, polyethylene, ethylene vinyl acetate, a copolymer thereof, or a blend thereof. In some embodiments of the present systems, the patient-interface layer includes an adhesive configured to couple the patient-interface layer to the tissue.

In some embodiments of the present systems, the first manifold comprises a foam or a non-woven textile. In some embodiments of the present systems, the first manifold comprises polyethylene, a polyolefin, a polyether, polyurethane, a co-polyester, a copolymer thereof, or a blend thereof.

In some embodiments of the present systems, the gas-occlusive layer comprises polyurethane, polyethylene, polyvinyl acetate, polyvinyl chloride, polyvinylidene chloride, isobutylene, a halogenated isomer, a copolymer thereof, or a blend thereof.

In some embodiments of the present systems, the sidewall of the container is gas-occlusive. In some embodiments of the present systems, the sidewall comprises polyurethane, polyethylene, polyvinyl acetate, polyvinyl chloride, polyvinylidene chloride, isobutylene, a halogenated isomer, a copolymer thereof, or a blend thereof.

Some embodiments of the present methods comprise coupling any of the present dressings to a patient's tissue; coupling the dressing to a container, wherein the container comprises: a sidewall that defines a chamber configured to be in fluid communication with the interior volume of the dressing; and an oxygen-generating material disposed within the chamber of container and configured to release oxygen when exposed to water; introducing oxygen into the interior volume of the dressing.

Some embodiments of the present methods comprise exposing the oxygen-generating material to water to introduce oxygen into the interior volume of the dressing.

In some embodiments of the present methods, the chamber of the container includes one or more capsules, each of which define a pocket that includes water, and the method comprises flexing at least one of the one or more capsules to release water from within the pocket and to expose the oxygen-generating material to water.

In some embodiments of the present methods, the introduction of oxygen into the interior volume of the dressing is performed via a conduit including: an elongated core comprising a third manifold having a foam or a non-woven textile; and a sheath comprising a gas-occlusive film; wherein the sheath is disposed around and extends along at least a majority of a length of the core. In some embodiments of the present methods, the third manifold comprises a hydrophilic material, optionally, a superabsorbent polymer. In some embodiments of the present methods, the third manifold comprises polyethylene, a polyolefin, a polyether, polyurethane, a co-polyester, a copolymer thereof, or a blend thereof. In some embodiments of the present methods, the sheath comprises polyurethane, polyethylene, polyvinyl acetate, polyvinyl chloride, polyvinylidene chloride, isobutylene, a halogenated isomer, a copolymer thereof, or a blend thereof. Some embodiments of the present methods comprise, prior to introducing oxygen into the interior volume of the dressing, reducing pressure within the interior volume.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or or. The phrase "and/or" includes any and all combinations of one or more of the associated listed items. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, an apparatus that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures. Figures having schematic views are not drawn to scale.

DETAILED DESCRIPTION

Figure 1:
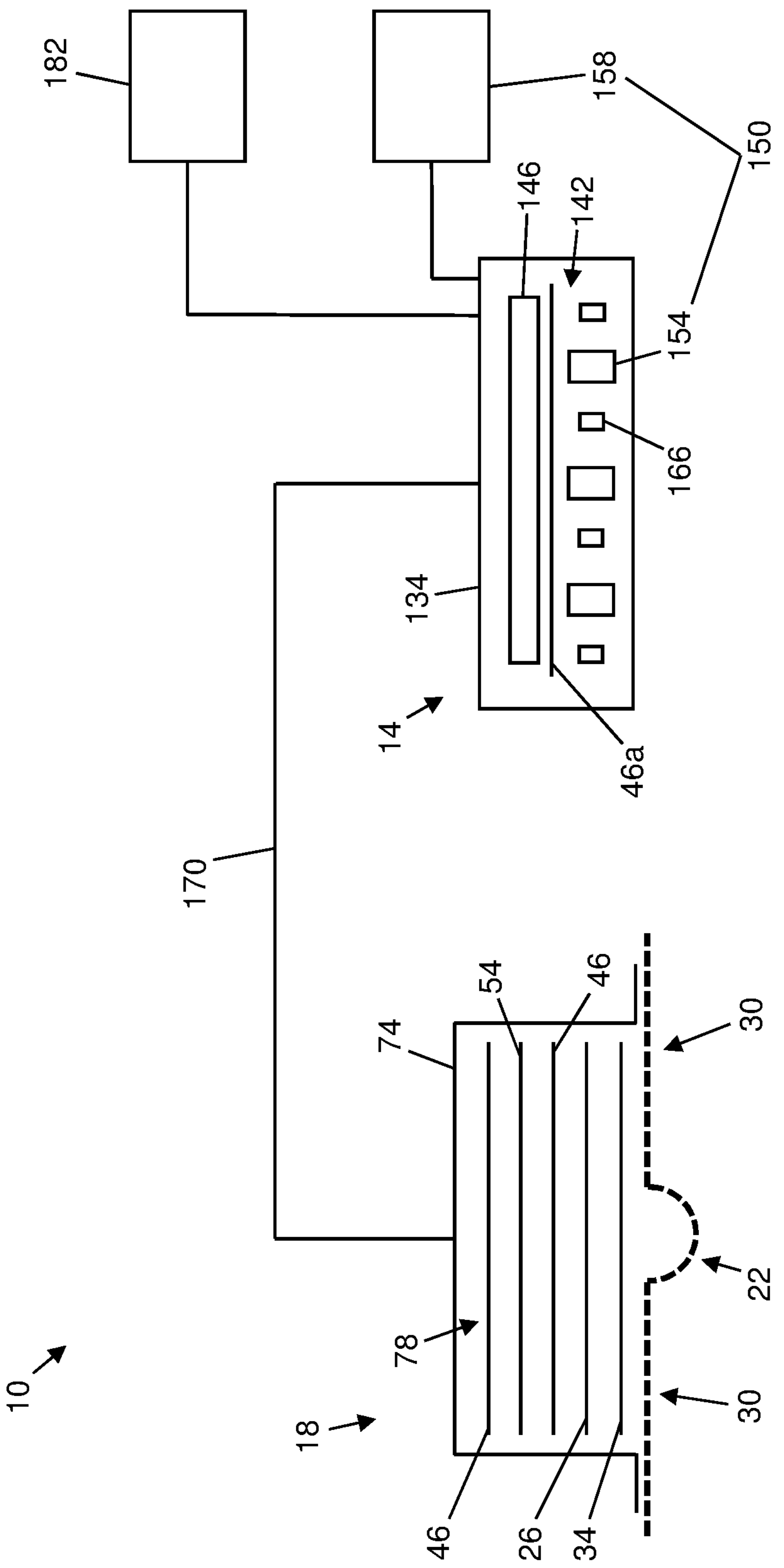
FIG. 1 is a schematic view of a first embodiment of the present systems.

Referring to FIG. 1, shown therein and designated by the reference numeral 10 is one embodiment of the present systems for providing topical wound therapy. System 10 includes an oxygen-generating device 14 and a wound dressing 18 for facilitating delivery of oxygen from the oxygen-generating device to a target tissue 22.

The term "target tissue" as used herein can broadly refer to a wound, a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The term "target tissue" as used herein can also refer to areas of tissue that are not necessarily wounded or exhibit a disorder, but include tissue that would benefit from tissue generation. The term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft.

Dressing 18 can include a patient-interface layer 26 configured to be in contact with target tissue 22 and/or tissue 30 surrounding the target tissue. For example, patient-interface layer 26 may be disposed over target tissue 22 and be in contact with tissue 30 surrounding the target tissue. For further example, patient-interface layer 26 may be disposed over target tissue 22 such that the patient-interface layer fills at least a portion of a recess defined by the target tissue. Patient-interface layer 26 can comprise any suitable planform shape, planform area, thickness, and/or the like that is appropriate to treat target tissue 22.

Patient-interface layer 26 can comprise an adhesive configured to couple the patient-interface layer to target tissue 22 and/or tissue 30 surrounding the target tissue. Such an adhesive can be configured to have low tack properties to minimize patient discomfort and/or tissue trauma as a result of the application, repositioning, and/or removal of patient-interface layer 26 from target tissue 22 and/or tissue 30 surrounding the target tissue. Such an adhesive may comprise any suitable adhesive, such as, for example, an acrylic adhesive, polyurethane gel adhesive, silicone adhesive, hydrogel adhesive, hydrocolloid adhesive, a combination thereof, and/or the like. Dressing 18 may include a protective liner 34 configured to be disposed on a surface of patient-interface layer 26 such that the protective liner at least partially covers the adhesive (e.g., prior to application of the dressing onto tissue).

Patient-interface layer 26 can comprise a plurality of openings 38 configured to allow communication of oxygen and exudate through the patient-interface layer and/or to promote granulation of target tissue 22. As shown, each of openings 38 of patient-interface layer 26 includes a circular shape. Openings 38 of patient-interface layer 26 can comprise any suitable shape, such as, for example, circular, elliptical, or otherwise round, square, rectangular, hexagonal, or otherwise polygonal. Each of openings 38 of patient-interface layer 26 may be substantially equal in size (e.g., as measured by a maximum transverse dimension of the opening), such as, for example, approximately any one of, or between approximately any two of, the following: 0.1, 0.2, 0.3, 0.4, 0.5, 0.75, 1.0, 1.25, and 1.5 centimeters (cm). In some embodiments, a patient-interface layer (e.g., 26) may comprise openings (e.g., 38) having different sizes (see FIG. 7).

Patient-interface layer 26 can comprise a plurality of gas passageways 42 defined by any suitable material, such as, for example, an open-cell foam (e.g., reticulated foam). Each gas passageway 42 can comprise a maximum transverse dimension of 400 and 600 micrometers. Patient-interface layer 26 can be hydrophilic. For example, patient-interface layer 26 can be configured to wick away (e.g., by capillary flow through gas passageways 42) exudate from target tissue 22 and/or tissue 30 surrounding the target tissue.

Patient-interface layer 26 can comprise any suitable material, such as, for example, a polymer, optionally, silicone, a hydrogel, polyvinyl alcohol, polyethylene, a polyurethane, polyether, ethylene vinyl acetate, a copolymer thereof, or a blend thereof. In some embodiments, a patient-interface layer (e.g., 26) can serve as or include a scaffold to promote tissue generation.

Such a scaffold may comprise any suitable scaffold for soft tissue healing, such as, for example, autograft tissue, collagen, polylactic acid (PLA), polyglycolic acid (PGA), and/or the like. In some embodiments, a patient-interface layer (e.g., 26) may comprise a biodegradable material, such as, for example, PLA, PGA, a polycarbonate, polypropylene fumarate, polycaprolactone, a polymeric blend thereof, and/or the like.

Non-limiting examples of patient-interface layer 26 include Silbione® HC2 products, which are commercially available from Bluestar Silicones International, of Lyon, France, and Nanova™ Dressing Perforated Silicone Wound Contact Layers, which are commercially available from Kinetic Concepts Inc., of San Antonio, Texas, USA.

Dressing 18 can include one or more manifolds 46. Each manifold 46 can be configured to allow communication of oxygen to target tissue 22 and/or allow communication of exudate to a sorbent material (e.g., 58) and/or to oxygen-generating device 14 (discussed in further detail below). For example, each manifold 46 can define a plurality of gas passageways 50 to distribute oxygen (e.g., from oxygen-generating device 14) across the manifold and/or to collect exudate from target tissue 22 across the manifold. Plurality of gas passageways 50 of each manifold 46 can be interconnected to improve distribution and/or collection of fluids across the manifold. For example, gas passageways 50 can be defined by an open-cell foam (e.g., reticulated foam), tissue paper, gauze, a non-woven textile (e.g., felt), and/or the like. In embodiments where manifold 46 comprises a non-woven textile, dressing 18 can comprise two or more manifolds 46 (e.g., one or more on either side of sorbent layer 54). Manifold 46 can comprise any suitable material, such as, for example, polyethylene, a polyolefin, a polyether, polyurethane, a co-polyester, a copolymer thereof, or a blend thereof. For example, in embodiments where manifold 46 comprises a foam, such a foam may be polyether-based polyurethane foam.

Manifold 46 can comprise any suitable planform shape, planform area, thickness, and/or the like that is appropriate to treat target tissue 22. In embodiments where manifold 46 comprises a non-woven textile, such a non-woven textile can comprise a density ranging from approximately 80 to 150 grams per square meter (GSM) and a thickness ranging from approximately 2 millimeters (mm) to 12 mm. In embodiments where manifold 46 comprises a foam, such a foam can comprise a porosity ranging from approximately 20 to 120 parts per million (ppm), such as, for example, 45 ppm, and a thickness ranging from approximately 2 mm to 12 mm, such as, for example, 6 mm.

Non-limiting examples of manifold 46 include MEDISPONGE® Foams, which are commercially available from Essentra PLC of Milton Keynes, England, and Exudate Management Systems, which are commercially available from TWE Group GmbH, of Emsdetten, Germany.

Figure 4:
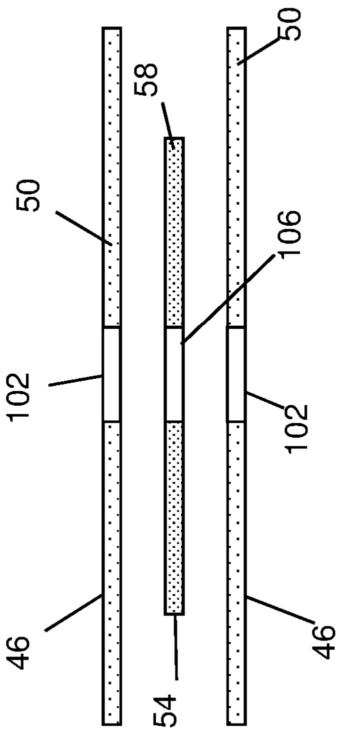
FIG. 4 is a cross-sectional side view of a portion of the dressing of FIG. 3, taken along line 4-4 of FIG. 3.

Dressing 18 can include a sorbent layer 54. Sorbent layer 54 can include a sorbent material 58 configured to capture exudate. As shown in FIG. 4, sorbent material 58 can be disposed below one of manifolds 46 and/or above another one of the manifolds. Sorbent layer 54, and, more particularly, sorbent material 58, can comprise any suitable adsorbent or absorbent material. Suitable examples of an absorbent material (e.g., a material that tends to swell, by 50 percent or more, due to the binding of liquid within the material) includes a foam, a non-woven textile, a superabsorbent polymer, and/or the like. For example, sorbent material 58 having absorbent material may comprise sodium carboxymethyl cellulose (NaCMC) fiber, alginate fiber, and/or the like. Suitable examples of an adsorbent material (e.g., a material that has a surface onto which liquid binds such that the material does not swell) include carbon filters, such as, for example, an activated charcoal filter and/or the like. Such an activated charcoal filter can be configured to remove nitrogen from therapeutic gas supplied from therapeutic gas source 14 into dressing 18. In this way and others, sorbent material 58 can facilitate the filtration of nitrogen within interior volume 78 of dressing 18.

Non-limiting examples of sorbent material 58 include superabsorbent wound care laminates having a density of 300 GSM, which are commercially available from Gelok International of Dunbridge, Ohio, USA, and Absorflex™, which has a density of 800 GSM and is commercially available from Texsus S.p.A. of Chiesina Uzzanese, Italy.

Figure 6:
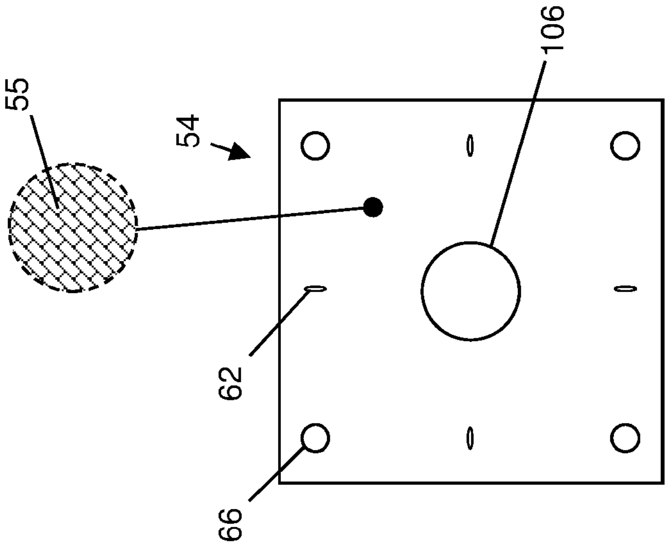
FIG. 6 is a top view of an embodiment of a sorbent layer, suitable for use in some embodiments of the present systems.

Sorbent layer 54 can comprise a plurality of perforations 62 and/or a plurality of openings 66, one or more of which are configured to allow fluid communication through the sorbent layer in instances where sorbent material 58 exhibits gel-blocking. Gel-blocking can occur when sorbent material 58 forms a gel in response to absorption of liquid. Gel-blocking can cause sorbent material 58 to block liquid and/or gas flow through the sorbent material. As shown in FIG. 6, sorbent layer 54 can comprise a textured surface having a plurality of grooves 55 configured to distribute liquid into and/or around sorbent material 58.

In this embodiment, each opening 66 may define an aperture comprising a planform area that does not substantially change (e.g., does not change by more than 5%) in response to fluid flow through the opening. Each perforation 62 may define an aperture comprising a planform area that substantially changes (e.g., changes by more than 5%) in response to fluid flow through the perforation. For example, one or more of perforations 62 may be defined by a slit in sorbent layer 54. Each of openings 66 of sorbent layer 54 may be substantially equal in size (e.g., as measured by a maximum transverse dimension of the opening), such as, for example, approximately any one of, or between approximately any two of, the following: 0.5, 0.75, 1.0, 1.25, and 1.5 cm. Each of perforations 62 of sorbent layer 54 may comprise a size (e.g., as measured by a maximum transverse dimension of the perforation) that is substantially smaller than the size of one or more of openings 66, such as, for example, 50, 60, 70, 80, or 90 percent smaller in size.

Figure 5:
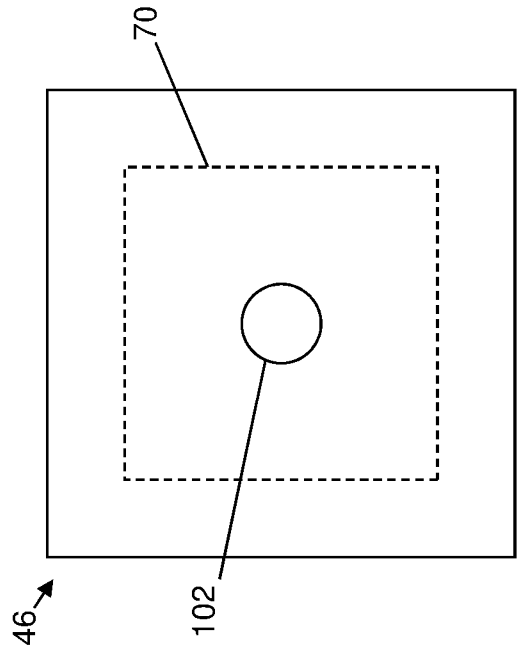
FIG. 5 is a top view of a portion of the dressing of FIG. 3.

Sorbent layer 54 can comprise any suitable planform shape, planform area, thickness, and/or the like appropriate to treat target tissue 22. As shown in FIG. 5, a planform area of sorbent layer 54 (depicted by dotted line 70) is smaller than a planform area of manifold 46 such that, when sorbent layer 54 is disposed between manifolds 46 on opposing sides of the sorbent layer, the opposing manifolds can be coupled around a peripheral edge of the sorbent layer. For example, the planform area of sorbent layer 54 is at least 5 percent smaller, such as, for example, 5, 10, 15, 20, 25, 30, 35, 40, or 45 percent smaller than the planform area of manifold 46. In this way and others, oxygen can circumvent sorbent layer 54 and be distributed across each manifold 46.

Dressing 18 can include a gas-occlusive layer 74. Gas-occlusive layer 74 can be configured to be disposed over one or more manifolds 46 and coupled to tissue 30 surrounding target tissue 22 such that an interior volume 78 is defined between the gas-occlusive layer and the target tissue and such that the gas-occlusive layer limits escape of oxygen and/or exudate from the interior volume between the gas-occlusive layer and the tissue surrounding the target tissue. A portion of gas-occlusive layer 74 can be coupled to tissue 30 surrounding target tissue 22 via patient-interface layer 26. To illustrate, a tissue-facing surface of gas-occlusive layer 74 can comprise an adhesive, such as, for example, an acrylic adhesive, polyurethane gel adhesive, silicone adhesive, a combination thereof, and/or the like, configured to couple the gas-occlusive layer to patient-interface layer 26 and/or tissue 30 surrounding target tissue 22. For example, when gas-occlusive layer 74 is coupled to patient-interface layer 26, such an adhesive may flow through one or more of openings 38 of the patient-interface layer to adhere gas-occlusive layer 74 to tissue 30 surrounding target tissue 22.

Gas-occlusive layer 74 can be sterile such that the gas-occlusive layer provides a viral and/or bacterial barrier to target tissue 22. Gas-occlusive layer 74 can be configured to provide a layer of protection from physical trauma to target tissue 22. In some embodiments, a portion of a gas-occlusive layer (e.g., 74) may be configured to be gas-permeable to provide a suitable (e.g., moist) wound healing environment and/or to prevent passive permeation of oxygen molecules through the gas-occlusive layer. Gas-occlusive layer 74 can comprise an oxygen permeability coefficient ($P \times 10^{10}$), at 25 degrees Celsius, ranging from 0.0003 and 0.5 (e.g., approximately any one of, or between approximately any two of the following: 0.0003, 0.0004, 0.0005, 0.0006, 0.0007, 0.0008, 0.0009, 0.001, 0.005, 0.01, 0.05, 0.1, 0.15, 0.2, 0.25, 0.3, 0.35, 0.4, 0.45, and 0.5), where P is measured in units of $[(cm^3)(cm)]/[(cm^2)(s)(cm\ Hg)]$ which represents [(amount of permeate)(gas-occlusive layer thickness)]/[(surface area)(time)(pressure-drop across the gas-occlusive layer)]. Gas-occlusive layer 74 can comprise a moisture vapor transmission rate (MVTR) of at least 250 grams per meters squared per day ($g/m^2$/day). In embodiments where a tissue-facing surface of gas-occlusive layer 74 comprises an adhesive (as discussed above), the adhesive may affect the gas permeability and/or the MVTR of the gas-occlusive layer. To illustrate, for a gas-occlusive layer (e.g., 74) having a film with a thickness of 0.025 mm and an adhesive with a thickness of 0.025 mm, the gas permeability and MVTR of the gas-occlusive layer are 50 percent of a gas permeability and MVTR of the same gas-occlusive layer without the adhesive.

Gas-occlusive layer 74 may comprise a flexible film, such as, for example, a hydrocolloid sheet. Gas-occlusive layer 74 can comprise any suitable material that limits escape of oxygen and/or exudate through the gas-occlusive layer, such as, for example, polyurethane, polyethylene, polyvinyl acetate, polyvinyl chloride, polyvinylidene chloride, isobutylene, a halogenated isomer, a copolymer thereof, or a blend thereof. Gas-occlusive layer 74 can comprise any suitable planform shape, planform area, thickness, and/or the like that is appropriate to treat target tissue 22. For example, gas-occlusive layer 74 can comprise a thickness that is approximately any one of, or between approximately any two of the following: 10, 15, 20, 25, 30, 35, 40, 45, 50, 55, and 60 micrometers.

Dressing 18 can comprise a valve 82 coupled to gas-occlusive layer 74. Valve 82 can be configured to permit communication of gas out of interior volume 78 through the valve and prevent communication of gas into the interior volume through the valve. For example, valve 82 can be configured to relief pressure within interior volume 78 when the pressure within the interior volume exceeds a threshold pressure. Such a threshold pressure may range from 8 to 24 mmHg (e.g., approximately any one of, or between approximately any two of the following: 8, 10, 12, 14, 16, 18, 20, 22, and 24 mmHg). Valve 82 can comprise any suitable one-way valve, such as, for example, a ball-check valve or a diaphragm check valve (e.g., defined at least in part by gas-occlusive layer 74). In this way and others, valve 82 can be configured to ensure that interior volume 78 does not become over-pressurized with oxygen (e.g., from oxygen-generating device 14) such that dressing 18 and tissue 30 surrounding target tissue 22 separate to allow oxygen therebetween.

Gas-occlusive layer 74 may comprise an oxygen sensor 86 configured to collect data indicative of the presence, volume, and/or concentration of oxygen within interior volume 78. Oxygen sensor 86 may comprise a display 90 configured to indicate, such as, for example, via a color change, the presence, volume, and/or concentration of oxygen within interior volume 78.

Dressing 18 may comprise a port 94 configured to be coupled to an opening 98 of gas-occlusive layer 74. Port 94 comprises one or more latching and/or interlocking features such that the port can be releasably coupled to oxygen-generating device 14. For example, port 94 can be configured to be releasably coupled to oxygen-generating device (e.g., 14), as discussed in further detail below, such that the oxygen-generating device can be decoupled from the port without removing dressing 18 from target tissue 22 and/or tissue 30 surrounding the target tissue.

Port 94 can be configured to allow fluid communication of oxygen and/or exudate between oxygen-generating device 14 and interior volume 78. More particularly, port 94 can be configured to allow communication of oxygen into interior volume 78 through the port and/or allow communication of exudate out of the interior volume through the port. A non-limiting example of port 94 includes the Sensa-T.R.A.C.™ Pad, which is commercially available from Kinetic Concepts Inc., of San Antonio, Texas, USA.

Dressing 18 can be configured such that port 94 can extend through one or more layers (e.g., 46, 54, and/or 74) of the dressing to guide communication of oxygen into interior volume 78 and promote circulation of the oxygen within the interior volume. For example, opening 98 of gas-occlusive layer 74 is configured to receive port 94. Manifold 46 can include an opening 102 positioned relative to the edges of the manifold such that, when port 94 is received by opening 98 of gas-occlusive layer 74, the port overlies at least a portion of the opening of the manifold. Opening 102 of manifold 46 can be configured to receive port 94 such that the port extends through the opening of the gas-occlusive layer and the opening of the manifold to guide the communication of oxygen into interior volume 78 of dressing 18. As shown in FIGS. 4 and 6, sorbent layer 54 can include an opening 106 positioned relative to the edges of the sorbent layer such that, when port 94 is received by opening 98 of gas-occlusive layer 74 and/or opening 102 of manifold 46, the port overlies at least a portion of the opening of the sorbent layer. Opening 106 of sorbent layer 54 can be configured to receive port 94 such that the port extends through the opening of the gas-occlusive layer, the opening of the manifold, and the opening of the sorbent layer to guide the communication of oxygen into interior volume 78 of dressing 18.

Figure 3:
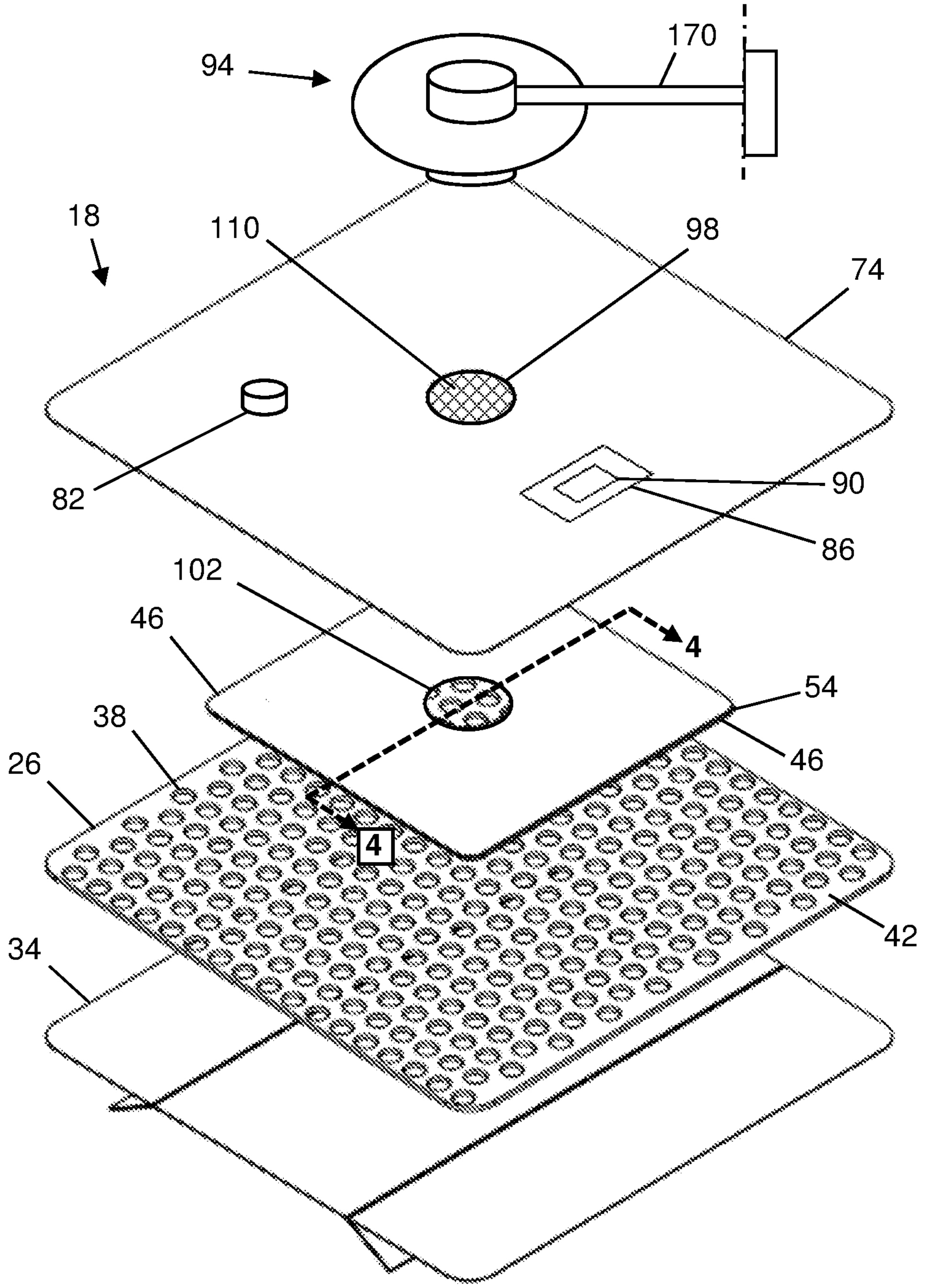
FIG. 3 is an exploded perspective view of a first embodiment of the present wound dressings, suitable for use in some embodiments of the present systems.

In this embodiment, dressing 18 comprises a filter 110 configured to filter fluid that flows through opening 98 of gas-occlusive layer 74. For example, filter 110 can be configured to provide a viral and/or bacterial barrier. As shown in FIG. 3, filter 110 comprises a layer of material that is bonded to a lower (e.g., tissue-facing) surface of gas-occlusive layer 74. In some embodiments, a filter (e.g., 110) comprises a layer of material that is bonded to an upper surface of a gas-occlusive layer (e.g., 74). In some embodiments, a filter (e.g., 110) comprises a layer of material that is bonded to a port (e.g., 94). Filter 110 can comprise any suitable material, such as, for example, polytetrafluoroethylene (PTFE) (e.g., an expanded PTFE), polyolefin, and/or the like. Filter 110 can comprise a backing material, such as, for example, a non-woven textile. Filter 110 may comprise a hydrophobic material. To illustrate, filter 110 can be configured to allow communication of oxygen into interior volume 78 through opening 98 of gas-occlusive layer, and thus, through port 94, and restrict communication of exudate out of the interior volume through the opening of the gas-occlusive layer, and thus, through the port. Filter 110 can comprise a pore size of approximately 0.05 to 0.15 micrometers (e.g., approximately any one of or between any two of the following: 0.05, 0.07, 0.09, 0.10, 0.11, 0.13, and 0.15 micrometers).

A non-limiting example of filter 110 includes GORE® Microfiltration Media for Medical Devices, which is commercially available from W. L. Gore & Associates, Inc., of Newark, Delaware, USA.

Figure 7:
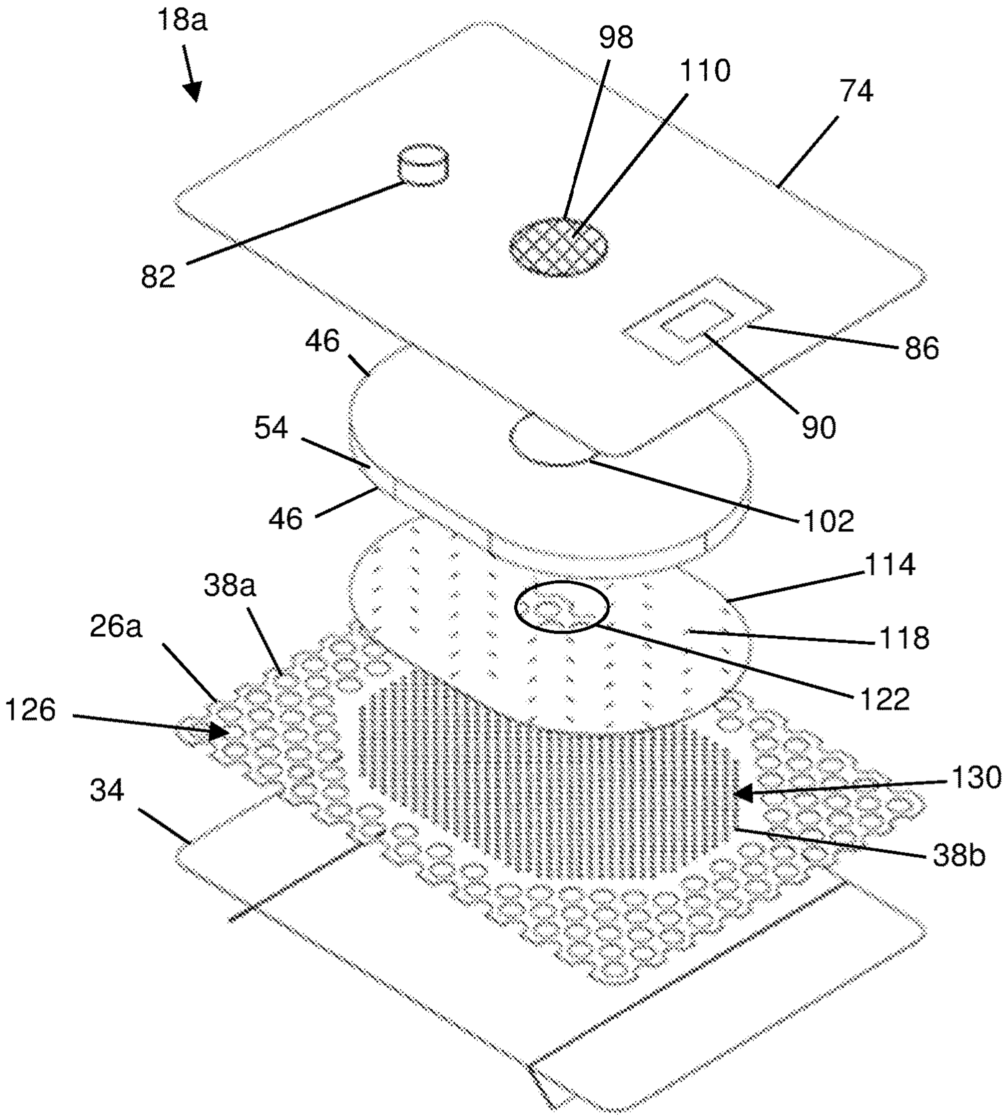
FIG. 7 is an exploded perspective view of a second embodiment of the present wound dressings, suitable for use in some embodiments of the present systems.
Figure 8:
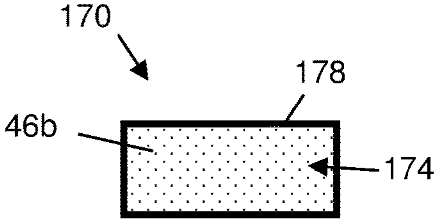
FIG. 8 is a cross-sectional end view of a portion of the system of FIG. 1, taken along line 8-8 of FIG. 2.

Referring now to FIG. 7, shown therein and designated by the reference numeral **18*a* is another embodiment of the present wound dressings for facilitating the delivery of oxygen to target tissue 22. Dressing 18*a* is substantially similar to dressing 18, with the primary exception that dressing 18*a* comprises a liquid control layer 114 configured to be disposed between manifold 46 and target tissue 22 to restrict communication of exudate toward the target tissue. In some embodiments, a liquid control layer (e.g., 114) can be disposed between a manifold (e.g., 46) and a sorbent layer (e.g., 54**).

Liquid control layer 114 can comprise a plurality of perforations 118 configured to permit exudate to flow away from target tissue 22 through the plurality of perforations and block the flow of exudate toward the target tissue through the plurality of perforations. Each perforation 118 may define an aperture comprising a planform area that changes (e.g., changes by more than 5%) in response to fluid flow through the perforation. Each of perforations 118 of sorbent layer 54 may be substantially equal in size (e.g., as measured by a maximum transverse dimension of the opening), such as, for example, approximately any one of, or between approximately any two of, the following: 1, 2, 3, 4, or 5 mm. For example, one or more of plurality of perforations 118 may comprise a slit.

Liquid control layer 114 can comprise any suitable material to restrict communication of exudate toward target tissue 22. For example, liquid control layer 114 can comprise a foam, a non-woven textile, and/or a film. For further example, liquid control layer 114 can comprise a hydrophilic material, such as, for example, a superabsorbent polymer.

Like manifold 46 and gas-occlusive layer 74, liquid control layer 114 can include an opening 122 positioned relative to the edges of the liquid control layer such that, when port 94 is received by opening 98 of gas-occlusive layer 74, opening 102 of manifold 46, and/or opening 106 of sorbent layer 54, the port overlies at least a portion of the opening of the liquid control layer. More particularly, port 94 can extend through opening 122 of liquid control layer 114 (e.g., in addition to extending through opening 98 of gas-occlusive layer 74, opening 102 of manifold 46, and opening 106 of sorbent layer 54) to guide the communication of oxygen into interior volume 78 of dressing **18*a***.

Dressing **18*a* includes a patient-interface layer 26*a*, which is substantially similar to patient-interface layer 26 with the exception that patient-interface layer 26*a* comprises a first portion 126 comprising a first plurality openings 38*a*, each having a first size (e.g., as measured by a maximum transverse dimension of the first opening, examples of which are provided above in relation to openings 38), and a second portion 130 comprising a second plurality of openings 38*b*, each having a second size (e.g., as measured by a maximum transverse dimension of the second opening) that is at least 50 percent (e.g., 50, 55, 65, 70, 75, 80, 85, 90, or 95 percent) smaller than the first size. For example, each of second plurality of openings 38*b*** may be substantially equal in size (e.g., as measured by a maximum transverse dimension of the opening), such as, for example, approximately any one of, or between approximately any two of, the following: 0.1, 0.2, 0.3, 0.4, and 0.5 cm.

In this embodiment, respective ones of second plurality of openings **38*b* of patient-interface layer 26*a* and respective ones of plurality of perforations 118 of liquid control layer 114 may be misaligned relative to each other to define a tortuous path for exudate flowing toward target tissue 22, thereby frustrating back flow of the exudate toward the target tissue. As shown in FIG. 7, patient-interface layer 26***a* can be configured to be disposed below liquid control layer 114.

Referring again to FIGS. 1 and 2, system 10 comprises oxygen-generating device 14. Oxygen-generating device 14 includes a container 134 that is disposed outside interior volume 78 of dressing 18. Container 134 can comprise any suitable storage device, such as, for example, a canister, pouch, sachet, bag, box, and/or the like.

Container 134 comprises a sidewall 138 that defines a chamber 142 configured to be in fluid communication with interior volume of dressing 18 (e.g., via a conduit 170). At least a portion of sidewall 138 of container 134 can be rigid or flexible. Sidewall 138 can be substantially similar to gas-occlusive layer 74. Sidewall 138 can comprise any suitable material that limits escape of oxygen and/or exudate through the sidewall, such as, for example, comprising polyurethane, polyethylene, polyvinyl acetate, polyvinyl chloride, polyvinylidene chloride, isobutylene, a halogenated isomer, a copolymer thereof, or a blend thereof. Like gas-occlusive layer 74, sidewall 138 can comprise an oxygen permeability coefficient ($P \times 10^{10}$), at 25 degrees Celsius, ranging from 0.0003 and 0.5 (e.g., approximately any one of, or between approximately any two of the following: 0.0003, 0.0004, 0.0005, 0.0006, 0.0007, 0.0008, 0.0009, 0.001, 0.005, 0.01, 0.05, 0.1, 0.15, 0.2, 0.25, 0.3, 0.35, 0.4, 0.45, and 0.5), where P is measured in units of $[(cm^3)(cm)]/[(cm^2)(s)(cm\ Hg)]$ which represents [(amount of permeate)(sidewall thickness)]/[(surface area)(time)(pressure-drop across the sidewall)]. Like gas-occlusive layer 74, sidewall 138 can comprise a moisture vapor transmission rate (MVTR) of at least 250 grams per meters squared per day ($g/m^2$/day).

Container 134 can be configured to be coupled to tissue 30 surrounding target tissue 22 in any suitable way, such as, for example, one or more adhesives described herein and/or one or more straps and/or interlocking or latching features.

System 10 comprises an oxygen-generating material 146 disposed within chamber 142 of container 134. Oxygen-generating material 146 is configured to release oxygen (e.g., a gas whose composition is approximately 99 or more percent oxygen) when exposed to water. Water, in this context, includes any substance having $H_2O$, such as, for example, exudate from target tissue 22 and/or water from a liquid source (e.g., 150). Oxygen-generating material 146 can comprise an adduct of hydrogen peroxide, such as, for example, sodium percarbonate and/or hydrogen peroxide-urea.

Liquid source 150 can comprise one or more capsules 154 configured to be disposed within chamber 142 of container 134. Each of capsules 154 defines a pocket that can include water. In this embodiment, flexion and/or breakage of a portion of at least one of capsules 154 can cause the capsule to release water from within the pocket. Capsules 154 can comprise any suitable material, such as, for example, polyethylene, polyether, polyurethane, a co-polyester, a copolymer, a blend thereof, or a foil film or laminate. Optionally, liquid source 150 can comprise a water reservoir 158 configured to be in fluid communication with chamber 142 of container 134 (e.g., via a conduit). As shown in FIG. 1, water reservoir 158 can be disposed outside of chamber 142 of container 134 and outside interior volume 78 of dressing 18.

Container 134 can be reusable. For example, after oxygen-generating material 146 has depleted and/or after liquid source 150 has been depleted, container 134 can be opened via a resealable opening 162 defined by sidewall 138 to allow access to chamber 142 such that the container can be refilled with additional oxygen-generating material and/or the liquid source can be refilled within additional water. In this way and others, container 134 reduces waste and expense associated with topical therapeutic oxygen wound therapy.

Container 134 may comprise a manifold 46*a*, which is substantially similar to manifold 46 of dressing 18. Manifold 46*a* can be disposed within chamber 142 of container 134. Oxygen-generating material 146 can be disposed above or below and coupled to manifold 46. For example, oxygen-generating material 146 can be coupled to manifold 46*a* by an adhesive. Manifold 46*a* can be configured to distribute and/or expose oxygen-generating material 146 to water.

System 10 can be configured to regulate the amount of water exposed to oxygen-generating material, thereby preventing oversaturation of the oxygen-generating material and limiting the rate and/or volume of oxygen emission.

For example, system 10 can comprise a competitive agent 166 disposed within chamber 142 of container 134 and configured to limit the communication of oxygen between the chamber of the container and interior volume 78 of dressing 18. Competitive agent 166 can comprise any suitable material that absorbs water, such as, for example, sodium carbonate, bentonite, and/or the like. In some embodiments, a competitive agent (e.g., 166) comprises an adhesive that bonds an oxygen-generating material (e.g., 146) to a manifold (e.g., 46*a*). In some embodiments, a competitive agent (e.g., 166) comprises a sorbent material, which is substantially similar to sorbent material 58 and is configured to capture water within a chamber (e.g., 142) of a container (e.g., 134). In some embodiments, a competitive agent (e.g., 166) comprises one or more valves within a container (e.g., 134) configured to provide water a tortuous flow path before being exposed to an oxygen-generating material (e.g., 146).

In some embodiments, a chamber (e.g., 142) of a container (e.g., 134) can comprise two or more sub-chambers (e.g., separated by a physical barrier, such as, for example, a weld, an adhesive, and/or the like), each comprising a discrete volume of an oxygen-generating material (e.g., 146) and/or a competitive agent (e.g., 166). Each of such sub-chambers can be exposed to water in sequence such that the oxygen-generating material (e.g., 146) within such a chamber (e.g., 142) is reacted in phases, rather than at once.

Figure 2:
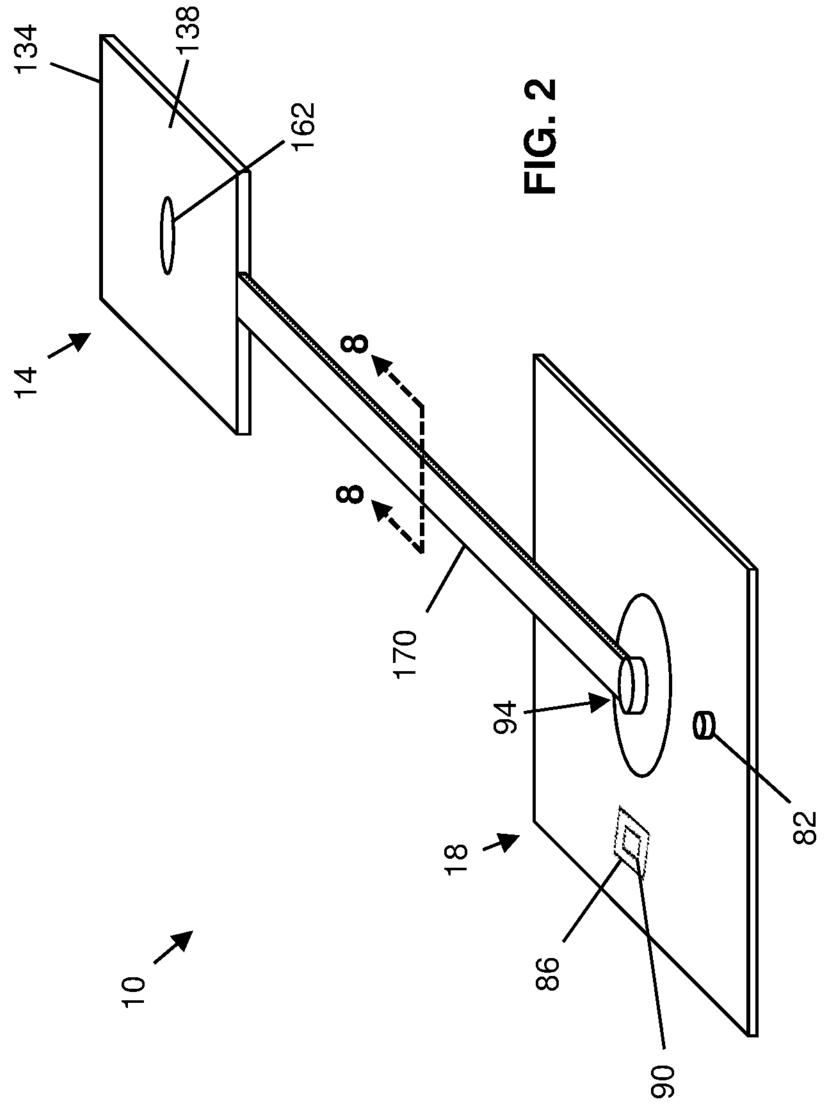
FIG. 2 is a perspective view of the system of FIG. 1, shown with some components omitted.

As shown in FIGS. 1 and 2, system 10 can include a conduit 170 configured to be coupled between container 134 and dressing 18 to permit fluid communication between chamber 142 of the container and interior volume 78 of the dressing. For example, port 94 can be configured to cooperate with conduit 170 to permit fluid communication between chamber 142 and interior volume 78.

Conduit 170 can be configured to be releasably coupled to port 94 and/or to container 134 (e.g., via a port on the container having one or more latching and/or interlocking features) such that the container can be decoupled from dressing 18 without removing the dressing from target tissue 22 and/or tissue 30 surrounding the target tissue.

Conduit 170 includes an elongated core 174 comprising a manifold 46*b*, which is substantially similar to manifold 46 of dressing 18. In this embodiment, manifold 46*b* can comprise a hydrophilic material, such as, for example, a superabsorbent polymer. Conduit 170 comprises a sheath 178 having a gas-occlusive film. Sheath 178 can be is disposed around and extend along at least a majority of a length of core 174. Sheath 178 can comprise any suitable material, such as, for example, polyurethane, polyethylene, polyvinyl acetate, polyvinyl chloride, polyvinylidene chloride, isobutylene, a halogenated isomer, a copolymer thereof, or a blend thereof.

Optionally, system 10 can comprise a negative pressure source 182 configured to be in fluid communication with chamber 142 of container 134 such that the negative pressure source removes fluid from and/or provides negative pressure within the chamber.

As used herein, "negative pressure" can refer to a pressure that is less than a local ambient pressure, such as less than atmospheric pressure, which can be measured outside interior volume 78 and/or outside chamber 142. "Negative pressure," as used herein, can also refer to a pressure less than a hydrostatic pressure experienced by target tissue 22. While the amount and nature of negative pressure applied within system 10 may vary according to therapeutic requirements, the negative pressure is generally a low vacuum (e.g., ranging approximately −5 millimeters of mercury (mmHg) to approximately −500 mmHg, and, more particularly, approximately −25 to −200 mmHg). Unless otherwise indicated, values of pressure stated herein are gauge pressures.

Negative pressure source 182 can comprise a reservoir of gas held within the reservoir at a negative pressure. Negative pressure source 182 may comprise a mechanical and/or electrically-powered device, such as, for example, a vacuum pump, a suction pump, a wall suction port, a micro-pump, and/or the like that can reduce pressure within dressing 18, conduit 170, and/or container 134. Negative pressure source 182 may comprise a housing configured to hold one or more components (e.g., one or more sensors, processing units, alarm indicators, displays, controllers, and/or the like) for controlling the negative pressure source and/or facilitating therapy.

By providing a negative pressure within chamber 142 of container 134, negative pressure source 182 can cause exposure of exudate to oxygen-generating material 146 within the chamber at least because the negative pressure source encourages the exudate to flow out of interior chamber 142 of dressing 18 (e.g., through conduit 170) and into the chamber of the container.

In some embodiments, a negative pressure source (e.g., 182) can be coupled to a dressing (e.g., 18) such that the negative pressure source encourages oxygen within a chamber (e.g., 142) of a container (e.g., 134) to flow into an interior volume (e.g., 78) of the dressing. In some embodiments, a negative pressure source (e.g., 182) can be coupled to a conduit (e.g., 170) such that the negative pressure source encourages oxygen within a chamber (e.g., 134) of a container (e.g., 134) to flow toward an interior volume (e.g., 78) of a dressing (e.g., 18) and/or encourages exudate within the interior volume of the dressing to flow toward the chamber of the container.

Negative pressure source 182 can comprise one or more user input interfaces (e.g., control knobs, buttons, dials, and/or the like) configured to allow a user to manipulate negative pressure characteristics within system 10. Beneficially, negative pressure source 182, and thus, such user input interfaces, can be disposed proximate to a site of application of the negative pressure (e.g., dressings 18 and 18*a*, container 134, and/or conduits 170 and 170*a*).

Figure 9:
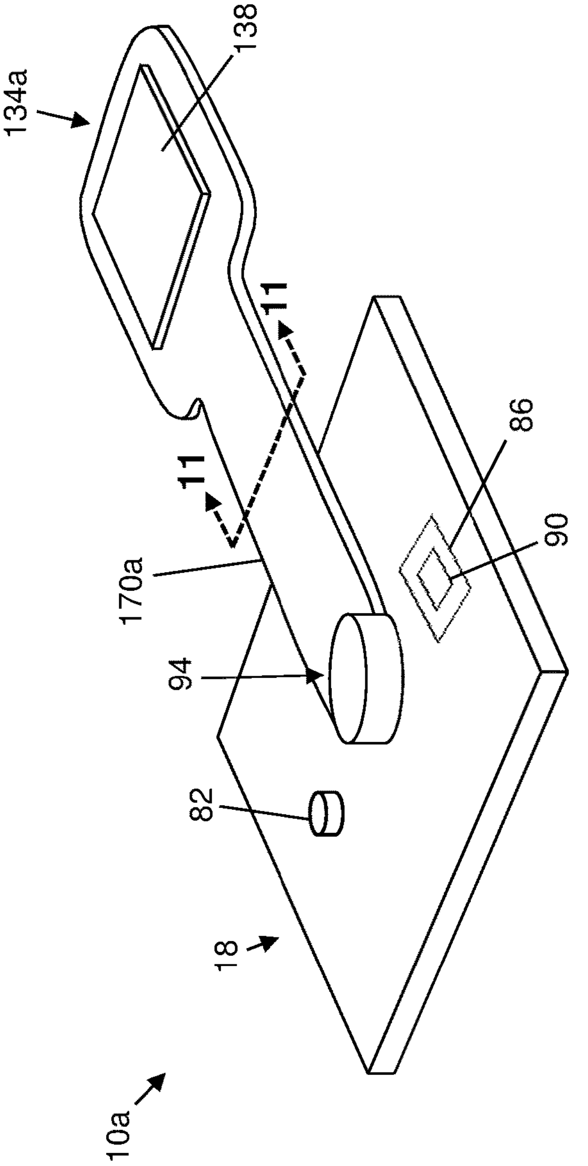
FIG. 9 is a perspective view of a second embodiment of the present systems.
Figure 11:
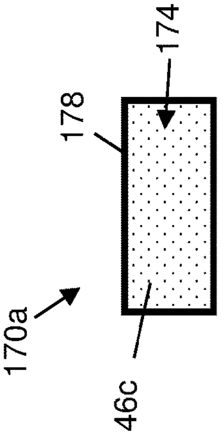
FIG. 11 is a cross-sectional end view of a portion of the system of FIG. 9, taken along line 11-11 of FIG. 9.
Figure 10:
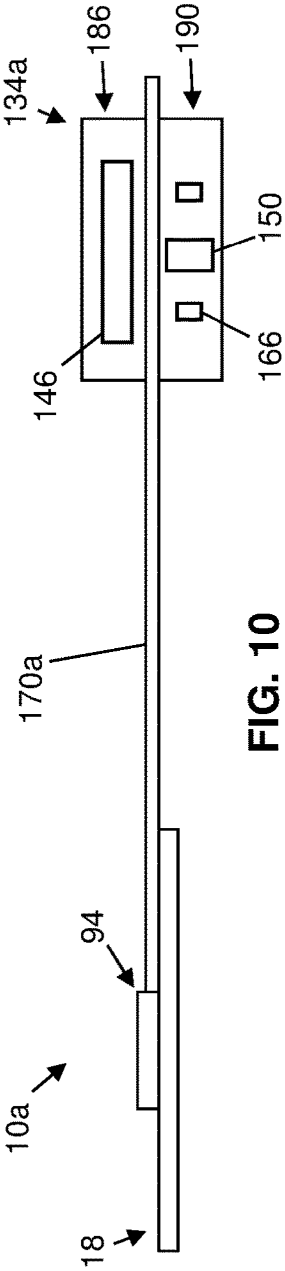
FIG. 10 is a schematic side view of the system of FIG. 9.

Referring now to FIG. 9, shown therein and designated by the reference numeral 10*a* is another embodiment of the present systems. In this embodiment, system 10*a* includes a conduit 170*a* that is substantially similar to conduit 170 with the exception that conduit 170*a* is unitary with a container 134*a*.

In this embodiment, container 134*a* includes a first portion 186 and a second portion 190. First portion 186 of container 134*a* includes oxygen-generating material 146 and second portion 190 of the container includes liquid source 150 and competitive agent 166. As shown in FIG. 9, system 10*a* includes a manifold 46*c*, which is substantially similar to manifold 46 with the exception that manifold 46*c* extends between conduit 170*a* and container 134*a* and divides the container into first portion 186 and second portion 190. Like manifold 46*a*, manifold 46*c* can be configured to distribute and/or expose oxygen-generating material 146 within first portion 186 of container 134*a* to water within second portion 190 of the container.

Some embodiments of the present methods comprise coupling one of the present dressings (e.g., 18, 18*a*) a patient's tissue (e.g., 22, 30), coupling the dressing to a container (e.g., 134, 134*a*), wherein the container comprises: a sidewall (e.g., 138) that defines a chamber (e.g., 142) configured to be in fluid communication with an interior volume (e.g., 78) of the dressing; and an oxygen-generating material (e.g., 146) disposed within the chamber of the container and configured to release oxygen when exposed to water; and introducing oxygen into the interior volume of the dressing.

In some embodiments, the method comprises exposing the oxygen-generating material (e.g., 146) to water to introduce oxygen into the interior volume (e.g., 78) of the dressing (e.g., 18, 18*a*). In some embodiments, the chamber (e.g., 142) of the container (e.g., 134, 134*a*) includes one or more capsules (e.g., 154), each of which define a pocket that includes water, and the method comprises flexing at least one of the one or more capsules to release water from within the pocket and to expose the oxygen-generating material to water. In some embodiments, the introduction of oxygen into the interior volume (e.g., 78) of the dressing (e.g., 18, 18*a*) is performed via a conduit (e.g., 170, 170*a*) including: an elongated core (e.g., 174) comprising a manifold (e.g., 46*b*, 46*c*) having a foam or a non-woven textile; and a sheath (e.g., 178) comprising a gas-occlusive film; wherein the sheath is disposed around and extends along at least a majority of a length of the core. In some embodiments, the manifold (e.g., 46*b*, 46*c*) of the conduit (e.g., 170, 170*a*) comprises a hydrophilic material, optionally, a superabsorbent polymer. In some embodiments, the manifold (e.g., 46*b*, 46*c*) comprises polyethylene, a polyolefin, a polyether, polyurethane, a co-polyester, a copolymer thereof, or a blend thereof. In some embodiments, the sheath (e.g., 178) comprises polyurethane, polyethylene, polyvinyl acetate, polyvinyl chloride, polyvinylidene chloride, isobutylene, a halogenated isomer, a copolymer thereof, or a blend thereof. In some embodiments, prior to introducing oxygen into the interior volume (e.g., 78) of the dressing (e.g., 18, 18*a*), the method comprises reducing pressure within the interior volume.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A dressing for facilitating delivery of oxygen to target tissue, the dressing comprising:

a manifold that defines a plurality of gas passageways and is configured to allow communication of oxygen to the target tissue;

a liquid control layer having a plurality of apertures having a planform area that changes in response to fluid flow, the liquid control layer configured to be disposed between the manifold and the target tissue to restrict communication of exudate toward the target tissue;

a patient-interface layer configured to be disposed below the manifold and in contact with the tissue surrounding the target tissue, the patient-interface layer defining a plurality of openings configured to allow communication of oxygen and exudate through the patient-interface layer, the plurality of openings misaligned with the plurality of apertures of the liquid control layer;

a gas-occlusive layer configured to be disposed over the manifold and coupled to tissue surrounding the target tissue such that:

an interior volume is defined between the gas-occlusive layer and the target tissue; and the gas-occlusive layer limits escape of oxygen from the interior volume between the gas-occlusive layer and the tissue surrounding the target tissue; and a port coupled to the gas-occlusive layer, wherein the port is configured to be releasably coupled to an oxygen-generating device and to allow fluid communication of oxygen between the oxygen-generating device and the interior volume.

2. The dressing of claim 1, wherein the port is configured to be releasably coupled to the oxygen-generating device such that the oxygen-generating device can be decoupled from the port without removing the dressing from the tissue surrounding the target tissue.

3. The dressing of claim 1, wherein the port is configured to allow communication of oxygen into the interior volume through the port and allow communication of exudate out of the interior volume through the port.

4. The dressing of claim 1, comprising a filter coupled to the gas-occlusive layer and configured to allow communication of oxygen into the interior volume through the port and restrict communication of exudate out of the interior volume through the port.

5. The dressing of claim 1, comprising a sorbent layer having a sorbent material configured to be disposed above or below the manifold and to capture exudate.

* * * * *